US012605197B2

(12) United States Patent
Lundstrom et al.

(10) Patent No.: US 12,605,197 B2
(45) Date of Patent: Apr. 21, 2026

(54) ELECTROSURGICAL GENERATOR CONTROL USING DYNAMIC PROCESS VARIABLES

(71) Applicant: Intuitive Surgical Operations, Inc., Sunnyvale, CA (US)

(72) Inventors: Forrest R. Lundstrom, Sunnyvale, CA (US); Rajeshwari Srinivasan, San Carlos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 726 days.

(21) Appl. No.: 17/891,811

(22) Filed: Aug. 19, 2022

(65) Prior Publication Data

US 2023/0056328 A1 Feb. 23, 2023

Related U.S. Application Data

(60) Provisional application No. 63/235,537, filed on Aug. 20, 2021.

(51) Int. Cl.
| | |
|---|---|
| *A61B 18/12* | (2006.01) |
| *A61B 18/14* | (2006.01) |
| *A61B 18/00* | (2006.01) |

(52) U.S. Cl.
CPC .......... *A61B 18/1206* (2013.01); *A61B 18/14* (2013.01); *A61B 2018/00648* (2013.01); *A61B 2018/00827* (2013.01); *A61B 2018/00875* (2013.01); *A61B 2018/00892* (2013.01)

(58) Field of Classification Search
CPC .......... A61B 2018/00648; A61B 2018/00702; A61B 2018/00779; A61B 2018/00827; A61B 2018/00875; A61B 2018/00892; A61B 18/1206; A61B 18/14; A61B 18/1442

See application file for complete search history.

(56) References Cited

U.S. PATENT DOCUMENTS

| | | | | |
|---|---|---|---|---|
| 2005/0203504 | A1* | 9/2005 | Wham | A61B 18/1442 606/34 |
| 2017/0333109 | A1* | 11/2017 | Gilbert | A61B 18/1206 |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

*Primary Examiner* — Michael F Peffley
*Assistant Examiner* — Samantha M Good
(74) *Attorney, Agent, or Firm* — Schwegman, Lundberg & Woessner, P.A.

(57) ABSTRACT

An electrosurgical system includes an RF output stage configured to impart RF power between first and second electrodes; measurement circuitry measures current and voltage imparted between the first and second electrodes; a processing circuit calculates power and impedance, based upon the measured current and the measured voltage; the processing circuitry uses a proportional-integral-derivative control loop to control RF power imparted between the electrodes, based upon a selected one of the measured current, the measured voltage, calculated power, and the calculated impedance.

17 Claims, 6 Drawing Sheets

600

602

DETERMINE
$V(t)_{NORMALIZED}$

604

DETERMINE
$I(t)_{NORMALIZED}$

606

DETERMINE
$P(t)_{NORMALIZED}$

ELECTROSURGICAL GENERATOR CONTROL USING DYNAMIC PROCESS VARIABLES

CLAIM OF PRIORITY

This application claims the benefit of priority under 35 U.S.C. § 119(e) to U.S. Provisional Patent Application Ser. No. 63/235,537, filed on Aug. 20, 2021, which is incorporated by reference herein in its entirety.

BACKGROUND

An electrosurgical signal generator (ESG) delivers power to biological tissue during medical procedures such as tissue cutting or tissue sealing. During a normal operational mode, an ESG imparts voltage across tissue and imparts current flow through the tissue at a prescribed power level. An ESG ordinarily can be configured according to different operational modes to impart energy at different power levels according to different protocols for different medical procedures and for different types of biological tissue.

A closed loop control system typically is used to control ESG operation. During normal operation, the control loop controls the ESG to maintain voltage, current, and power parameters within prescribed ranges according to a selected operational mode. Tissue impedance generally changes during cutting or sealing procedures due to tissue desiccation, for example. A change in tissue impedance can cause corresponding changes in voltage across the tissue and in current flow through the tissue. The control loop controls the ESG to deliver a prescribed power to tissue under changing tissue impedance according to the operational mode.

Short circuit events sometimes occur during a medical procedure that can result in current spikes or arcs that can cause injury to a patient or damage to the instrument that is in contact with the patient Open circuit events sometimes occur during a medical procedure that can result in excessive leakage current that can cause injury to the patient or user. During aberrant conditions such as a short circuit event or an open circuit event, the control loop controls the ESG to temporarily interrupt delivery of energy during the aberrant condition so as to avoid or to at least minimize patient injury and instrument damage.

In a typical earlier ESG, output power control generally involves repeated measurement of voltage, current, and power at a rate in the KHz frequency range. The power level at which a typical ESG delivers energy to cut or seal tissue during a medical procedure generally is controlled through control of voltage and/or current delivered to the tissue. Since tissue impedance ordinarily changes during the procedure, the voltage and/or current delivered to the tissue ordinarily must be adjusted to maintain a predetermined cutting or sealing energy delivery power level. A typical earlier ESG control loop compared error values for multiple different parameters such as power, current, voltage, and leakage current to determine necessary adjustments to current and/or voltage delivered to tissue to maintain a predetermined power delivery to tissue, despite changes in tissue impedance. Since these error values are not directly comparable, heuristic gain calculations often were used to compare errors. However, heuristic gain calculations to compare error values generally required additional processing circuit cycles and often required manual setting of several gain terms for each of the errors. The processing circuit cycles and manual settings added delay to the complexity of use of the ESG.

SUMMARY

In one aspect, an electrosurgical system is provided that includes a first electrode and a second electrode. An RF output stage is configured to impart RF power between the first and second electrodes. Current measurement circuitry is configured to measure current, at a sampling rate, imparted between the first and second electrodes. Voltage measurement circuitry is configured to measure voltage, at the sampling rate, imparted between the first and second electrodes. A processing circuit is configured to perform operations that include calculating power imparted between the first and second electrodes, based upon the measured current and the measured voltage. The operations include calculating impedance between the first and second electrodes, based upon the measured current and the measured voltage. The operations include using a proportional-integral-derivative (PID) control loop to control RF power imparted between the electrodes, based upon a selected one of the measured current, the measured voltage, and the calculated power.

In another aspect, a method is provided to control an electrosurgical generator that imparts RF power between a first electrode and a second electrode. Current imparted between the first and second electrodes is measured at a sampling rate. Voltage imparted between the first and second electrodes is measured at the sampling rate. Power imparted between the first and second electrodes is calculated based upon the measured current and the measured voltage.

Impedance between the first and second electrodes is calculated based upon the measured current and the measured voltage. A proportional-integral-derivative control loop to is used control RF power imparted between the electrodes, based upon a selected one of the measured current, the measured voltage, and the calculated power. The selected one of the measured current, the measured voltage, and the calculated power is selected for use by the proportional-integral-derivative control loop, based at least in part upon the calculated impedance.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

Figure 1:
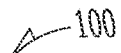
FIG. 1 is an illustrative block diagram of an example monopolar electrosurgical system.
Figure 1:
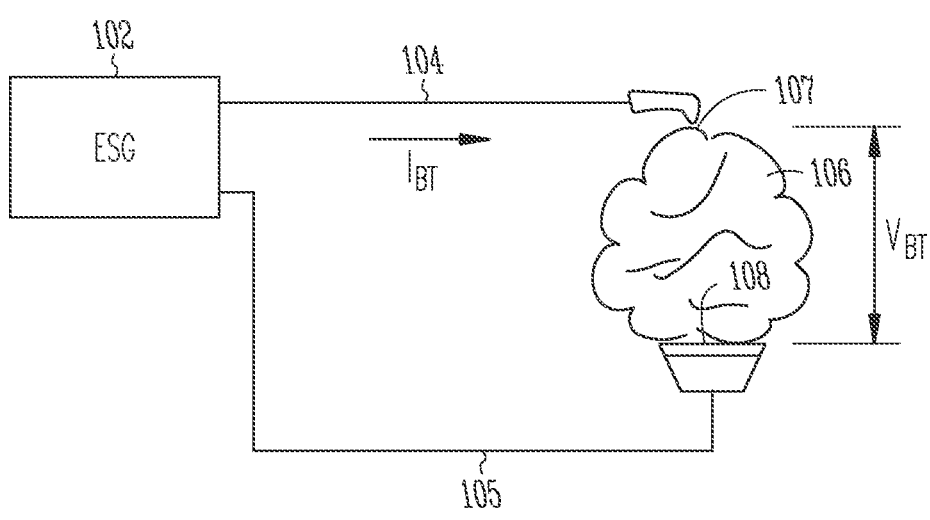

FIG. 1 is an illustrative block diagram of an example monopolar electrosurgical system 100. The monopolar electrosurgical system 100 includes an electrosurgical signal generator (ESG) 102, a first, active electrode 107, and a second, return electrode 108. A first conductor 104 electrically couples the ESG 102 to the active electrode 107. A second conductor 105 electrically couples the ESG 102 to the return electrode 108. During a medical procedure, a patient's biological tissue 106 is electrically coupled between the active electrode 106 and the return electrode 108 while the ESG 102 imparts RF power to the biological tissue 106 to achieve a clinical effect such as tissue cutting and/or tissue sealing. A clinician can manually manipulate the active electrode 107 to selectively contact different portions of the patient's biological tissue 106 that are targeted for treatment. The return electrode 108 is fixedly attached to a non-target portion of the patient tissue 106, that is not subjected to treatment, that is displaced away from the targeted tissue. RF current flows from the ESG 102 to the active electrode 107 and to the target tissue. The RF current flows from the active electrode 107 to the target tissue, and from the target tissue through biological 106, to the non-target tissue. The RF current flows from the non-target tissue to the return electrode 108 and back to the ESG 102. The active electrode typically has a small enough tissue contact surface area to concentrate heat energy for maximum clinical effect such as for cutting and/or sealing at the target tissue portion. Whereas, the return electrode 108 typically has a large enough tissue contact surface area to distribute the return energy across a wide enough tissue area at the non-target tissue portion to avoid tissue damage and patient injury.

Figure 2:
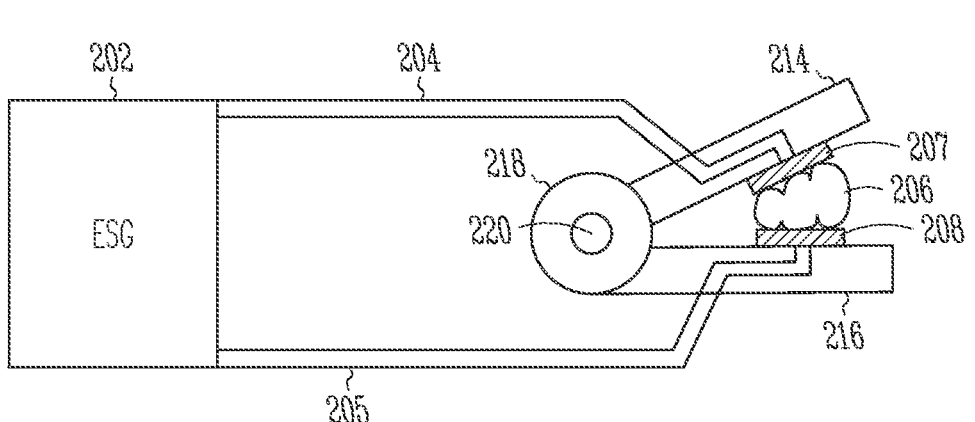
FIG. 2 is an illustrative block diagram of an example bipolar electrosurgical system.

FIG. 2 is an illustrative block diagram of an example bipolar electrosurgical system 200. The bipolar electrosurgical system 200 includes an electrosurgical signal generator (ESG) 202, first and second opposed jaws 214, 216 that include corresponding active and return electrodes 207 and 208, respectively. The jaws 214, 216 are mounted to a support structure 218 that includes a pivot axis 220. At least one of the jaws is pivotally mounted to the pivot axis 220 to be operable to rotate relative to the pivot axis 220 to transition the between an 'open' configuration in which the jaws 214, 216 are spaced farther apart from one another (not shown), and a 'closed' configuration in which the jaws 214, 216 are spaced closer together such that target biological tissue 206 can be grasped between them, as shown. A first conductor 204 electrically couples the ESG 202 to the active electrode 207. A second conductor 205 electrically couples the ESG to the return electrode 208. During a medical procedure, a patient's target biological tissue 206 is fixedly gripped between the first and second jaws 214, 216 such that the tissue is electrically coupled between the active electrode 207 and the return electrode 208. The ESG 202 imparts RF energy, which is delivered to the biological tissue 206 to achieve a clinical effect such as cutting and/or sealing. A clinician can manually adjust the grip from time to time to adjust the targeting of patient tissue for treatment. RF current flows from the ESG 202 on the first conductor 204 to the active electrode 207, through the biological tissue 206, to the return electrode 208 and back to the ESG 206 on the second conductor 205.

Figure 3:
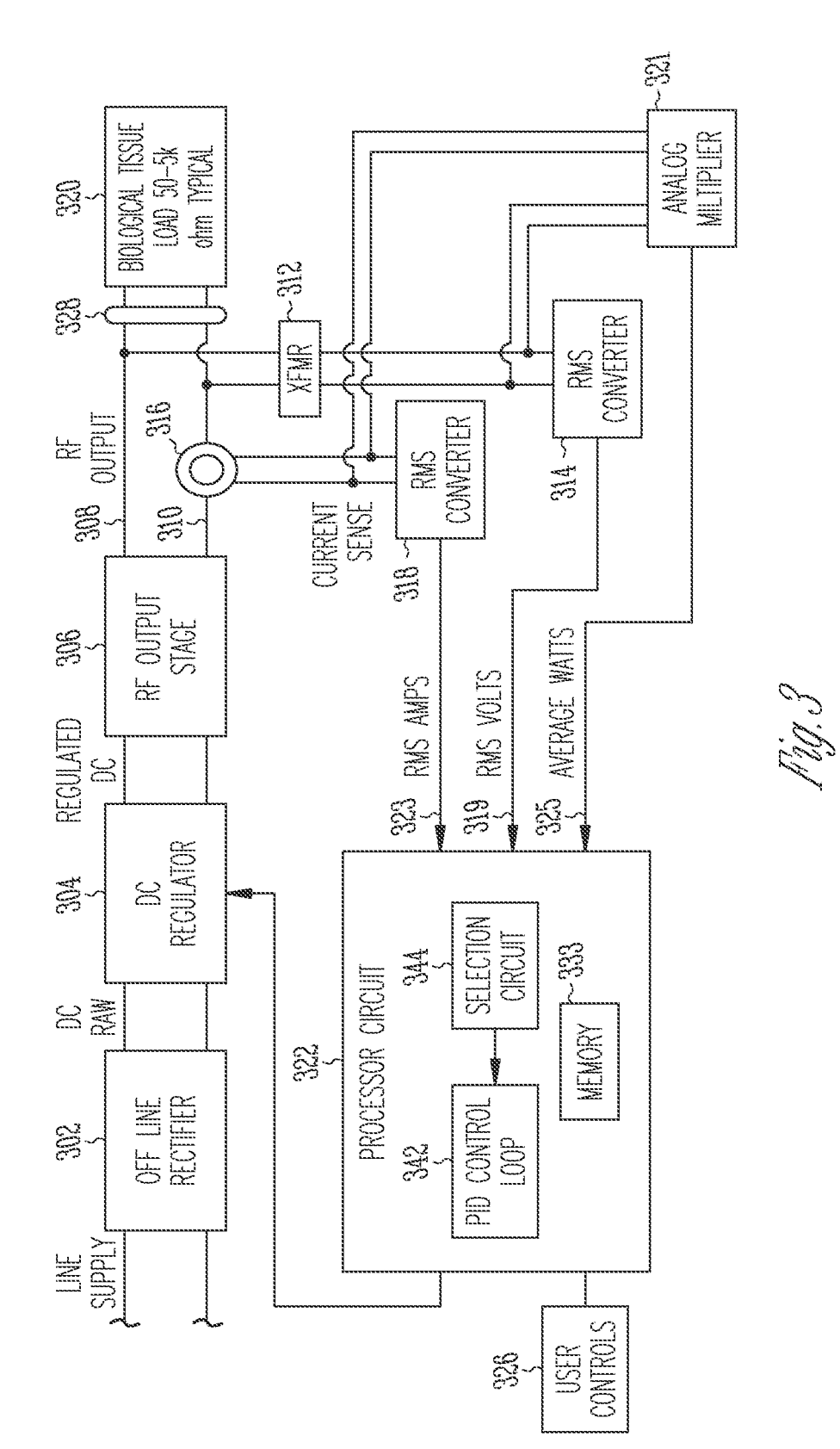
FIG. 3 is an illustrative block diagram representing an example electrosurgical signal generator.

FIG. 3 is an illustrative block diagram representing an example ESG 300. The ESG 300 includes a processor circuit 322 that is configured to implement a proportional-integral-differential (PID) control loop 342 and process variable selection circuit 344 and that includes non-transitory memory 333 to store program instructions and data, an off line rectifier 302 coupled to convert an AC line voltage signal to a raw rectified DC signal, a DC regulator 304 to convert the rectified DC voltage signal to a controlled DC voltage signal, and an RF output stage 306 coupled to convert the controlled DC voltage to high frequency output energy that can be applied across first and second output electrodes 308, 310 at a surgical instrument end effector (not shown). Voltage measurement circuitry includes a voltage transformer 312 and a first RMS converter 314 coupled to monitor an RF output voltage across the first and second output electrodes 308, 310 and to provide an RMS voltage value $v(t)_{RMS}$ via line 319 to the processor circuit 322. Current measurement circuitry includes a current sense transformer 316 and a second RMS converter 318 coupled to monitor an RF output current between the first and second output electrodes 308, 310 and to provide via line 323 an RMS current $i(t)_{RMS}$ to the processor circuit 322. Power measurement circuitry includes an analog multiplier circuit 321 coupled to determine a DC representation of the instantaneous mean real power value $p(t)_{MEAN}$ delivered by the ESG system, based the instantaneous RMS voltage value $v(t)_{RMS}$ and the instantaneous RMS current value $i(t)_{RMS}$ according to the relationship:

$$p(t)_{MEAN} = v(t)_{RMS} \times i(t)_{RMS} \tag{1}$$

The instantaneous mean real power value $p(t)_{MEAN}$ values is provided to the processor circuit 322. A user input control 326 is coupled to receive user input parameters to the processor circuit 322, which may include a maximum high frequency current, voltage or power, a target high frequency voltage, high frequency current or high frequency power, or some combination of these values, for example.

In operation, the first and second output electrodes 308, 310 may be located at a surgical instrument end effector 328 to contact two different locations on biological tissue 320. The RF output voltage may represent voltage across the biological tissue 320 between the first and second electrodes 308, 310 and the RF output current may represent current passing through the biological tissue 320 between the first and second electrodes 308, 310. In some examples, the first and second electrodes 308, 310. The first and second electrodes 308, 310 can be configured for use in a monopolar system as described with reference to FIG. 1. Alternatively, the first and second electrodes 308, 310 can be configured for use in a bipolar system as described with reference to FIG. 2. In general, the impedance load of a patient's biological tissue 320 typically can range from 50 to 5 k ohms, depending on the electrosurgical device used and tissues being targeted. The first RMS converter 314 converts a sensed RF output voltage signal to a first DC feedback signal indicating an RF output voltage level. The second RMS converter 318 converts the sensed RF output current signal to a second DC feedback signal indicating an RF output current level. The analog multiplier circuit 321 converts the sensed RF output voltage and the sensed RF output current to third DC feedback signal indicating average real RF output power.

The processor circuit 322 is configured to implement the PID control loop 342 that produces a feedback control signal $C_{FB}$ on control line 324, which is provided to the DC regulator 304. The PID controller produces the control signal based at least in part upon impedance between the active and return electrodes 308, 310 and at least one of the measured output voltage, the measured output current and the measured output power. The regulated DC output voltage level provided by the DC regulator 304 determines RF voltage and RF current delivered to the tissue by the RF output stage 306, which determines the RF power level power delivered to the tissue 320. An example PID control loop 342 is configured to produce a control signal to maintain a predetermined power delivery to the tissue despite changes in tissue impedance. The user input control 326 can be used by a clinician to adjust the predetermined power level.

Figure 4:
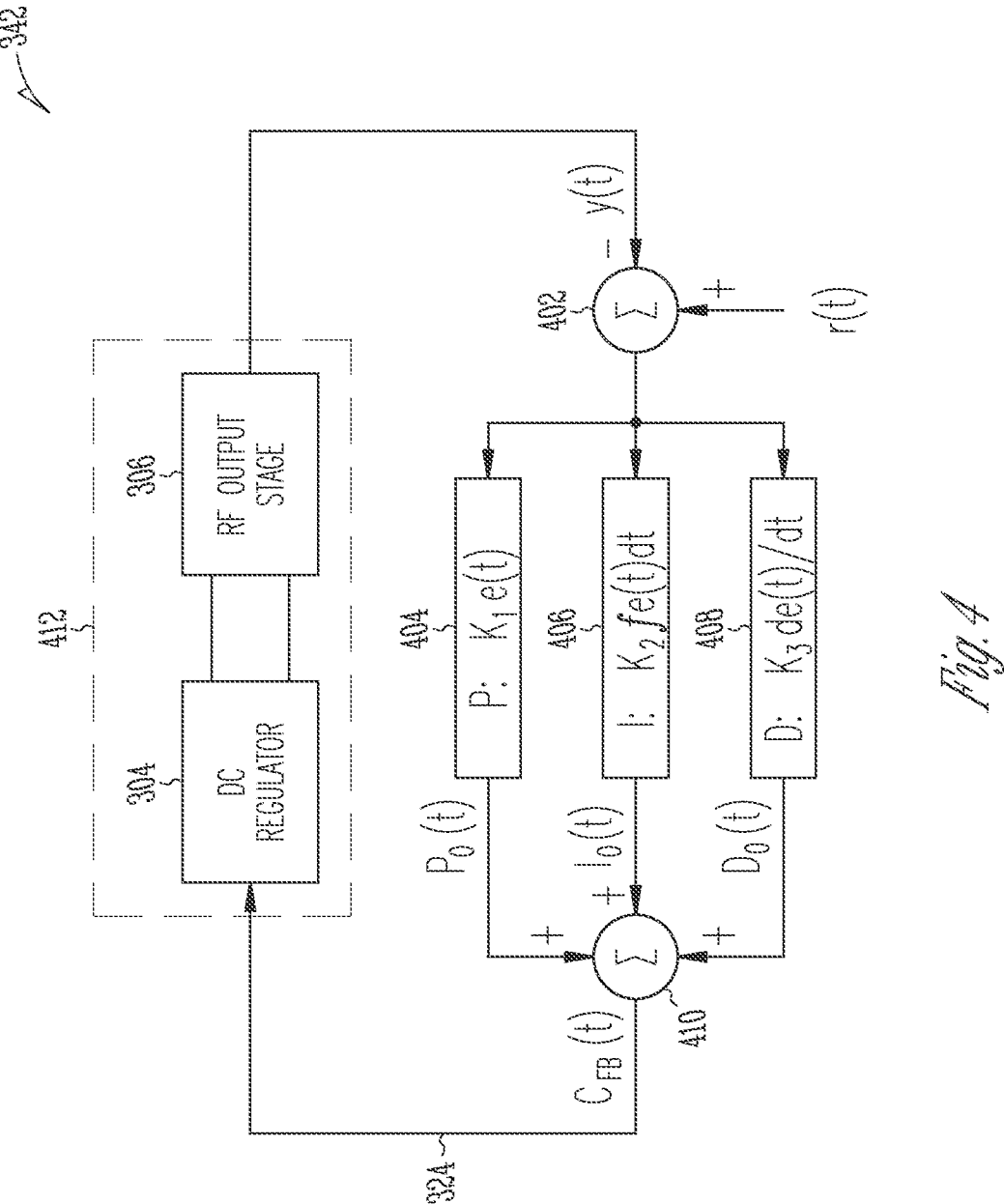
FIG. 4 is illustrative block diagram of an example Proportional-Integral-Derivative (PID) control loop.

FIG. 4 is illustrative block diagram of an example known proportional-integral-derivative (PID) control loop. An example processor circuit 322 includes a microcontroller circuit configured to implement the PID control loop 342 according to program instructions stored in the non-transitory computer readable storage device 333. An alternative example processor circuit 322 includes a field programmable gate array circuit (not shown) configured to implement at least a portion of the PID control loop 342. An example a PID control loop 342 produces a voltage feedback control signal $C_{FB}(t)$ on line 324 to control operation of the ESG 300 based upon a dynamically selectable process variable that includes a selected one of a voltage, a current, and a power. An example PID control loop 342 controls the voltage control signal on line 324 that causes the DC regulator 304 to produce the regulated DC voltage that is provided to the RF output stage 306. As explained more fully below, a set point is prescribed for each of the selectable process variables, voltage, current, and power. As used herein, a 'set point' refers to a desired or commanded value for a process variable. More specifically, a set point is prescribed for a voltage across the active and return electrodes 308, 310; a set point is prescribed for current flow between active and return electrodes 308, 310; and a set point is prescribed for power imparted across the active and return electrodes 308, 310 to biological tissue. A difference, referred to as an error, between a measured value of a selected process variable and the set point corresponding to that selected process variable is used by the PID control loop 342 to produce a control output used to reduce the error. In an example PID control loop 342, current, voltage, and power across the electrodes 308, 310 is repeatedly measured at a prescribed loop rate to continually adjust the feedback control signal on line 324 in response to changes in impedance between the electrodes 308, 310. Significantly, as explained more fully below, the process variable selection for use by the PID control loop 342 can be updated continuously during a medical procedure in response to changes of impedance between the electrodes 108, 110.

An example PID control loop 342 includes an error computation circuit 402 that determines an error value e(t), based upon a difference between a selected process variable y(t) and a set point r(t) corresponding to the selected process variable. As explained more fully below, the selected process variable can be one of voltage, current, or power. In an example PID control loop 342, the error computation circuit 402 comprises a subtraction circuit that subtracts a measured value of a selected process variable value y(t) from a corresponding set point value r(t) to produce the error value e(t) for the selected process variable. A proportional computation circuit block produces 404 a proportional output component value P(t) based upon the error value e(t) and a proportional gain ($K_1$), which determines a ratio of proportional output response $P_O(t)$ to the error signal. An integration computation circuit block sums 406 the error term e(t) over time to produce an integral output component $I_O(t)$. An integral component value increases over time unless the error is zero, so the effect is to drive the steady-state error to zero. A derivative computation circuit block 408 determines a derivative output component $D_O(t)$ that is proportional to the rate of change of the selected process variable y(t). The value of the derivative output component decreases if the process variable is increasing rapidly. The derivative output component $D_O(t)$ adjusts to cause the control loop 342 to react either more or less strongly to changes in the error term based upon the rate of change of the selected process variable. Graham C. Goodwin et al., Control System Design, Chapter 6, Classical PID Control, pages 159-175, Pearson Indian Education, 2015, describes a typical PID control loop A combiner circuit 410 combines the proportional, integral, and derivative output components $P_O(t)$, $I_O(t)$, $D_O(t)$ to produce a feedback control signal $C_{FB}(t)$ for input to RF power delivery process 412 being controlled. In an example PID control loop 342, the combiner circuit 410 comprises a summation circuit that adds together the proportional, integral, and derivative outputs $P_O(t)$, $I_O(t)$, $D_O(t)$ to produce the feedback control signal $C_{FB}(t)$, which corresponds to the voltage control signal on line 324.

Figure 5:
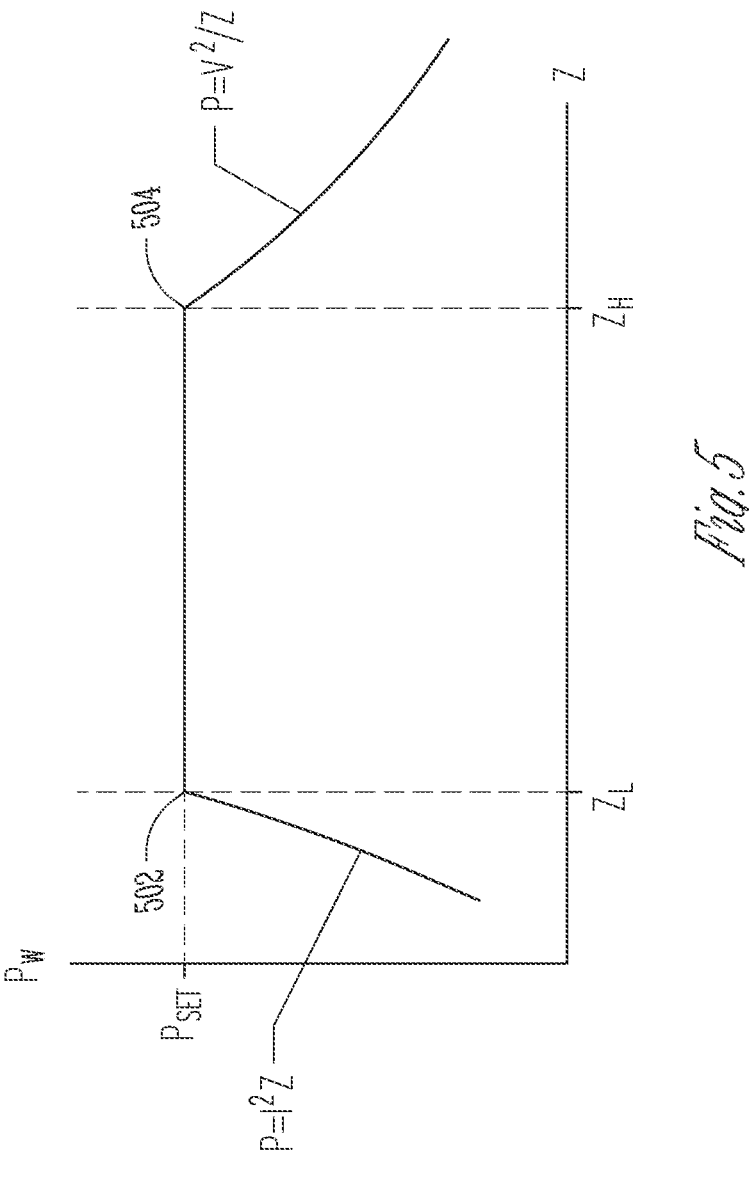
FIG. 5 is an example curve that pictorially represents control function parameters used by a PID control loop to control an electrosurgical process.

FIG. 5 is an example control function curve 500 that pictorially represents control function parameters used by an example PID control loop 342 to control an electrosurgical process. The control function parameters represented by the curve 500 are stored in the memory device 333. The user controls 126 can be used to receive user input to configure control function parameters such as to select set points for voltage, current, and power, for example. The example control function curve has power $P_W$ on a vertical axis and impedance Z on a horizontal axis. During a medical procedure, e.g., cutting or sealing, the ESG is configured to control an electrosurgical process that uses RF power to impart heat energy to biological tissue at a predetermined power. In a typical example electrosurgical process, the constant power is selected to be 50 Watts, although other power levels in a range (5 W-120 W) generally can be used. In some example electrosurgical processes, energy may be imparted at different predetermined power levels during different stages of the process. However, during each stage, energy typically is imparted at a constant predetermined power. Thus, for example, power delivery during each stage may be represented by a different corresponding control function curve.

The example control function curve 500 determines a power set point parameter $P_{SET}$, a current set point parameter $I_{SET}$, and a voltage set point parameter $V_{SET}$. The power set point parameter is $P_{SET}$ is selected to deliver energy to tissue at a constant prescribed power level, e.g., 50 W, throughout a range of impedance values. The current set point $I_{SET}$ corresponds to a lower impedance value within the prescribed constant impedance value range, also referred to herein as the 'left shoulder' portion 502 of the control function curve 500. The voltage set point $V_{SET}$ corresponds to a higher impedance value within the prescribed constant impedance value range, also referred to herein as the 'right shoulder' portion 504 of the control function curve 500.

More particularly, the current set point $I_{SET}$ is selected to be a current value at an intersection of a curve represented as, $P=I^2Z$, for a first lower prescribed value of Z, $Z=Z_L$, at which $P_W=P_{SET}$. The first lower value of $Z_L$ can be selected to be a value indicative of an actual or imminent short circuit condition. In an example ESG, a first lower prescribed value for $Z_L$ is selected to be about 100 ohms.

The voltage set point $V_{SET}$ is selected to be a voltage value at an intersection of a curve represented as, $P=V^2/Z$, for a second higher prescribed value of Z, $Z=Z_H$, at which $P_W=P_{SET}$. The second higher value of $Z_H$ can be selected to be a value indicative of an open circuit condition. A second higher prescribed value for $Z_H$ is selected to be about 3,000 ohms for a monopolar electrosurgical system, for example. A second higher prescribed value for $Z_H$ is selected to be about 600 ohms for a bipolar electrosurgical system, for example.

During an electrosurgical procedure, a clinician can cause an active terminal of an ESG system to electrically contact biological tissue, either directly or through a surface effect, to achieve a clinical effect such as cutting or sealing. During such contact, the PID control loop 342 controls a selected process variable y(t) (one of $v(t)_{RMS}$, $i(t)_{RMS}$, $p(t)_{MEAN}$) to achieve delivery of energy at a prescribed constant power level. During an electrosurgical procedure, a short circuit condition can occur that causes the power delivery according to the relationship $P=I^2Z$. A short circuit may occur, for example, due to the active and return electrodes 308, 310 contacting one another, due to electrical arcing, or due to contact between an electrode and an external metal object such as a surgical staple. Conversely, during an electrosurgical procedure, an open circuit condition can occur that causes power delivery according to the relationship $P=V^2/Z$. An open circuit can occur, for example, when a clinician moves an active electrode so as to not contact tissue such as when the clinician is repositioning the active terminal. Moreover, a prescribed reference impedance $Z_R$ on the impedance versus poser curve 500 is determined based upon $Z_H$ and $Z_L$. In example curve 500, the prescribed reference impedance $Z_R$ is selected as a midpoint impedance $Z_{MP}$ between $Z_L$ and $Z_H$ according to the relationship, $$Z_{MP}=(Z_L+Z_H)/2 \qquad (2)$$

Figure 6:
FIG. 6 is an example measurement parameter normalization procedure.
Figure 6:
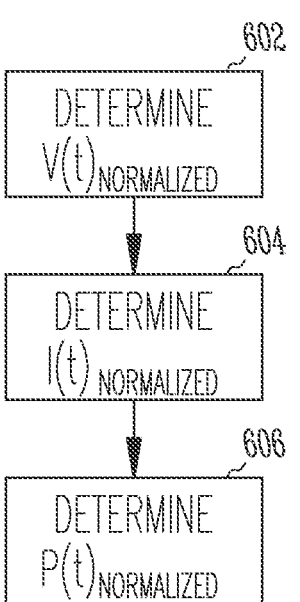

FIG. 6 is an example measurement parameter normalization procedure 600. Values for voltage, current and power values are normalized so that they can be compared directly as explained more fully below. The example processor circuit 322 is configured according to program instructions stored in a non-transitory computer readable storage device 333 to perform operations to compute the normalized values.

Operation 602 determines a normalized voltage value $v(t)_{Normalized}$, based upon the voltage set point $V_{SET}$ and the measured RMS voltage value $v(t)_{RMS}$, according to the relationship, $$v(t)_{Normalized}=1-v(t)_{RMS}/v_{SET} \qquad (3)$$

Operation 604 determines a normalized current value $i(t)_{Normalized}$, based upon the current set point $I_{SET}$ and the measured RMS current value $i(t)_{RMS}$, according to the relationship, $$i(t)_{Normalized}=1-i(t)_{RMS}/ISET \qquad (4)$$

Operation 606 determines a normalized power value $p(t)_{Normalized}$, based upon the power set point $P_{SET}$ and the measured power value $p(t)_{MEAN}$, according to the relationship, $$p(t)_{Normalized}=1-p(t)_{MEAN}/PSET \qquad (5)$$

Figure 7:
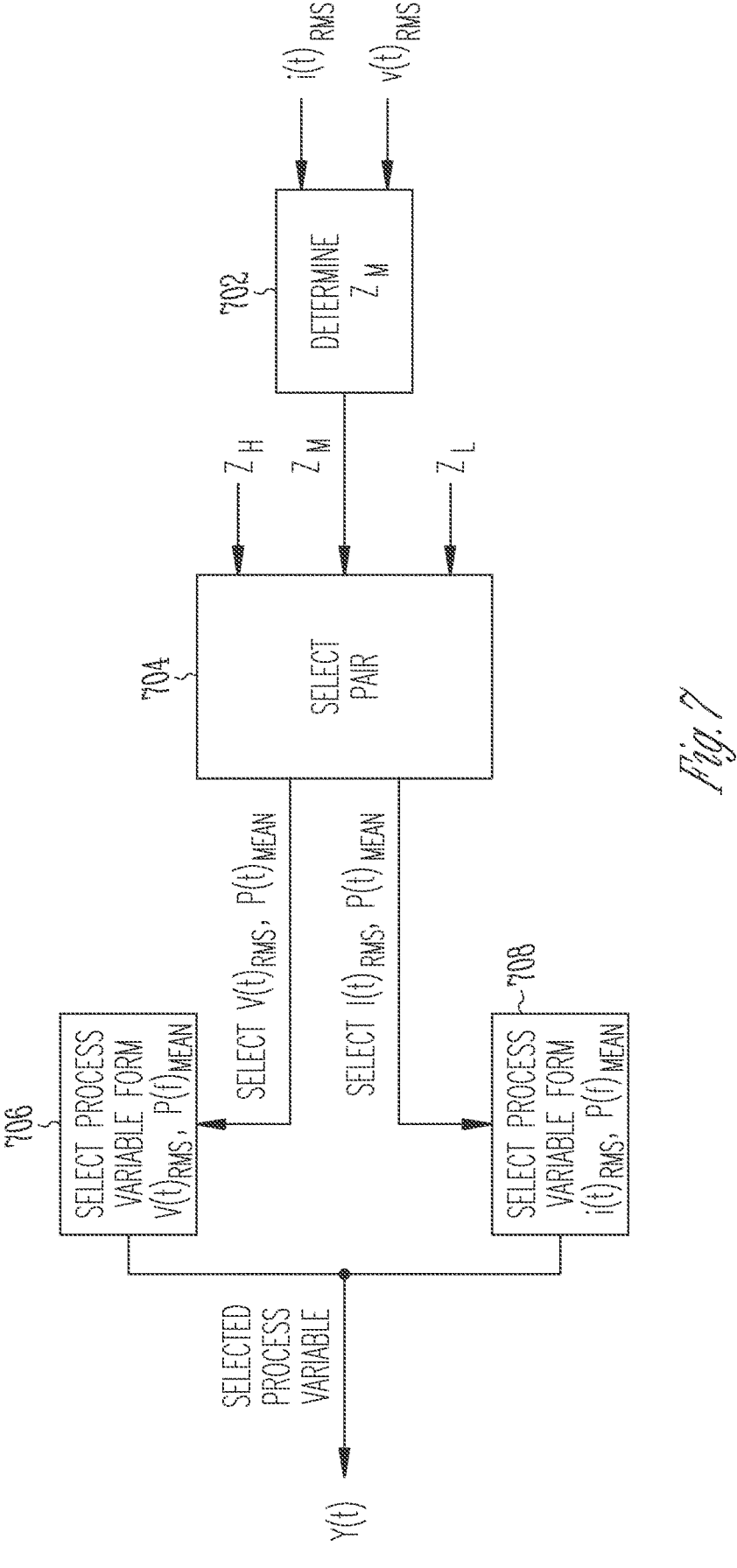
FIG. 7 is an illustrative functional flow diagram representing an example process variable selection procedure.

FIG. 7 is an illustrative functional flow diagram representing an example process variable selection procedure 700. The example processor circuit 322 is configured according to program instructions stored in a non-transitory computer readable storage device 333 to select a process variable y(t) (one of $v(t)_{RMS}$, $i(t)_{RMS}$, $p(t)_{MEAN}$) for use by the PID control loop 342. The selected process variable can be one or measured $v(t)_{RMS}$, measured $i(t)_{RMS}$ or calculated $p(t)_{MEAN}$. The example process variable selection procedure 700 runs at a sampling rate in a frequency range 1-20 KHz to dynamically select a process variable value that can be changed based at least in part upon changes in measured impedance measured impedance $Z(t)_{MEASURED}$. Values for $v(t)_{RMS}$, $i(t)_{RMS}$, $p(t)_{MEAN}$ and $Z(t)_{MEASURED}$, are determined at the sampling rate.

Operation 702 determines a measured instantaneous impedance $Z(t)_{MEASURED}$ according to the relationship, $$Z_{MEASURED}=v(t)_{RMS}/i(t)_{RMS} \qquad (6)$$

Operation 704 selects either a first candidate pair of process variables, $v(t)_{RMS}$ and $p(t)_{RMS}$, or a second candidate pair of process variables, $i(t)_{RMS}$ and $p(t)_{RMS}$ as candidates for use as a process variable within the PID control loop based at least in part upon the measured impedance $Z(t)_{MEASURED}$ and the reference point impedance $Z_R$. In an example procedure 700, the reference impedance is the midpoint impedance, and operation 704 selects a candidate pair based upon a difference between the measured impedance $Z(t)_{MEASURED}$ and midpoint point impedance Z. More particularly, operation 704 selects members of the first candidate pair, $v(t)_{RMS}$ and $p(t)_{RMS}$, to act as candidates for use as process variables in response to the measured impedance $Z(t)_{MEASURED}$ being greater than $Z_R$ and closer to $Z_H$ than to $Z_L$. Conversely, operation 704 selects members of the second candidate pair, $i(t)_{RMS}$ and $p(t)_{RMS}$, to act as candidates for use as process variables in response to the measured impedance $Z(t)_{MEASURED}$ being less than $Z_{MP}$. and closer to $Z_L$ than to $Z_H$.

In response to selection of the first pair, $v(t)_{RMS}$ and $p(t)_{MEAN}$, as process variable candidates at the operation 704, operation 706 selects one of $v(t)_{RMS}$ and $p(t)_{MEAN}$ to act as the process variable in the PID control loop 342, based upon the magnitudes of these two instantaneous normalized values. In response to the normalized voltage value, $v(t)_{Normalized}$, being less than the normalized power value, $p(t)_{Normalized}$, operation 706 selects $v(t)_{RMS}$ as the process variable and configures the PID control loop 342 to use $v(t)_{RMS}$ as the process variable, and to use $V_{SET}$ as the set point parameter (r(t)). Conversely, in response to the normalized power value, $p(t)_{Normalized}$, being less than the normalized voltage value, $v(t)_{Normalized}$, operation 706 selects $p(t)_{MEAN}$ as the process variable and configures the PID control loop 342, to use $p(t)_{MEAN}$ as the process variable, and to use $P_{SET}$ as the set point parameter (r(t)).

In response to selection of the second pair, $i(t)_{RMS}$ and $p(t)_{MEAN}$, as process variable candidates by the operation 704, operation 708 selects one of $i(t)_{RMS}$ and $p(t)_{MEAN}$ to act as the process variable in the PID control loop 342, based upon the magnitudes of these two instantaneous normalized values. In response to the normalized current value, $i(t)_{Normalized}$, being less than the normalized power value, $p(t)_{Normalized}$, operation 708 selects the current $i(t)_{RMS}$ as the process variable and configures the PID control loop 342 to use $i(t)_{RMS}$ as the process variable and to use $I_{SET}$ as the set point parameter (r(t)). Conversely, in response to the normalized power value, $p(t)_{Normalized}$, being less than the normalized current value, $i(t)_{Normalized}$, operation 708 selects $p(t)_{MEAN}$ as the process variable and configures the PID control loop 342 and to use $P_{SET}$ as the set point parameter (r(t)).

It will be appreciated that the procedures 600 and 700 is iterative. Values for $v(t)_{RMS}$, $i(t)_{RMS}$, $p(t)_{MEAN}$ and Z(t)

$_{MEASURED}$, are determined at the sampling rate and change over time. For example, in response to a change in measured impedance during sampling during a clinical procedure, operation 704 may adjust the candidate selection and select a different pair of candidates than was previously selected, and as a result, one or the other of operations 706 or 708 may adjust its process variable selection and select a different process variable for use during subsequent portions of the clinical procedure. Thus, the process variable selection can change dynamically with changes in measured impedance.

The ESG 300, therefore, dynamically selects a process variable y(t) based upon at least in part upon instantaneous measured impedance $Z(t)_{MEASURED}$. A different process variable can be selected according to the procedures of FIGS. 6-7 based upon changes in the measured impedance $Z(t)_{MEASURED}$. Moreover, a different process variable is selected based upon normalized values of $v(t)_{RMS}$, $i(t)_{RMS}$, and $p(t)_{MEAN}$, which obviates the need for complex heuristics, which can reduce processing cycles.

The above description is presented to enable any person skilled in the art to dynamically select process variable from among instantaneous voltage, current and power values for use by a proportional integral derivative control loop to control an electrosurgical generator during a medical procedure. Various modifications to the examples will be readily apparent to those skilled in the art, and the generic principles defined herein may be applied to other embodiments and applications without departing from the spirit and scope of the invention. In the preceding description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

The invention claimed is:

1. An electrosurgical system comprising:
a first electrode;
a second electrode;
an RF output stage configured to impart RF power between the first and second electrodes;
current measurement circuitry configured to measure current, at a sampling rate, imparted between the first and second electrodes;
voltage measurement circuitry configured to measure voltage, at the sampling rate, imparted between the first and second electrodes;
a processing circuit configured to perform operations including:
calculating power imparted between the first and second electrodes, based upon the measured current and the measured voltage;
calculating impedance between the first and second electrodes, based upon the measured current and the measured voltage;
using a proportional-integral-derivative control loop to control RF power imparted between the electrodes, based upon a selected one of the measured current, the measured voltage, and the calculated power; and
selecting the one of the measured current, the measured voltage, and the calculated power, based at least in part upon the calculated impedance and two or more of a normalized representation of a measured current value, a normalized representation of a measured voltage value, and a normalized representation of a calculated power value.

2. The electrosurgical system of claim 1,
wherein the processing circuit is further configured to perform operations including:
adjusting a selection of one of the measured current, the measured voltage, and the calculated power based upon a change in the calculated impedance.

3. The electrosurgical system of claim 1,
wherein calculating the power, imparted between the first and second electrodes based upon the measured current and the measured voltage includes calculating the power at the sampling rate; and
wherein the processing circuit is further configured to perform an operation including:
adjusting a selection of one of the measured current, the measured voltage, and the calculated power based upon a change in the calculated impedance.

4. The electrosurgical system of claim 3,
wherein calculating impedance between the first and second electrodes based upon the measured current and the measured voltage includes calculating impedance at the sampling rate.

5. The electrosurgical system of claim 1,
wherein the processing circuit is further configured to perform operations including:
calculating the normalized representation of the current value based upon the measured current value and a current set point;
calculating the normalized representation of the voltage value based upon the measured voltage value and a voltage set point;
calculating the normalized representation of the power value based upon the calculated power value and a power set point; and
selecting the one of the measured current, the measured voltage, and the calculated power based at least in part upon the calculated impedance and two or more of the normalized current value, the normalized voltage value and the normalized power value.

6. The electrosurgical system of claim 1, further including:
a DC voltage regulator circuit coupled to provide regulated DC power to the RF output stage;
wherein controlling power imparted between the electrodes includes controlling the regulated DC power provided by the DC voltage regulator circuit to the RF output stage.

7. The electrosurgical system of claim 1,
wherein the processing circuit includes a microcontroller; and further including:
a non-transitory storage device including instructions to configure to the microcontroller to perform the operations.

8. The electrosurgical system of claim 1,
wherein the processing circuit includes a field programmable gate array.

9. An electrosurgical system comprising:

a first electrode;

a second electrode;

an RF output stage configured to impart RF power between the first and second electrodes;

current measurement circuitry configured to measure current, at a sampling rate, imparted between the first and second electrodes;

voltage measurement circuitry configured to measure of voltage, at the sampling rate, imparted between the first and second electrodes;

a processing circuit configured to perform operations including:

calculating power imparted between the first and second electrodes, based upon the measured current and the measured voltage;

calculating impedance between the first and second electrodes, based upon the measured current and the measured voltage;

using a proportional-integral-derivative control loop to control RF power imparted between the electrodes, based upon a selected one of the measured current, the measured voltage, and the calculated power; and wherein selecting the one of the measured current, the measured voltage, and the calculated power includes:

comparing the calculated impedance with a reference impedance;

selecting one of a normalized current and a normalized voltage, based upon whether the calculated impedance is greater than or less than the reference impedance; and selecting between a normalized power and the selected one of the normalized current and the normalized voltage, based upon magnitudes of the normalized power and the selected one of the normalized current and the normalized voltage.

10. The electrosurgical system of claim 9, wherein the processing circuit is further configured to perform operations including:

associating a current set point with a first predetermined impedance value; and associating a voltage set point with a second predetermined impedance value;

wherein the reference impedance is a midpoint impedance between the first predetermined impedance value and the second predetermined impedance value.

11. The electrosurgical system of claim 9, wherein selecting the one of the measured current, the measured voltage, and the calculated power includes:

selecting between a normalized power and the selected one of the normalized current and the normalized voltage includes, selecting the lesser valued one of the normalized power, and the selected one of the normalized current and the normalized voltage.

12. A method to control electrosurgical generator that imparts RF power between a first electrode and a second electrode, comprising:

measuring current, at a sampling rate, imparted between the first and second electrodes;

measuring voltage, at the sampling rate, imparted between the first and second electrodes;

calculating power imparted between the first and second electrodes, based upon the measured current and the measured voltage;

calculating impedance between the first and second electrodes, based upon the measured current and the measured voltage;

using a proportional-integral-derivative control loop to control RF power imparted between the electrodes, based upon a selected one of the measured current, the measured voltage, and the calculated power;

selecting the one of the measured current, the measured voltage, and the calculated power for use by the proportional-integral-derivative control loop, based at least in part upon the calculated impedance; and selecting the one of the measured current, the measured voltage, and the calculated power, based at least in part upon the calculated impedance and two or more of a normalized representation of a measured current value, a normalized representation of a measured voltage value, and a normalized representation of a calculated power value.

13. The method of claim 12 further including:

adjusting a selection of one of the measured current, the measured voltage, and the calculated power based upon a change in the calculated impedance.

14. The method of claim 12 further including:

wherein calculating the calculate power, imparted between the first and second electrodes based upon the measured current and the measured voltage includes calculating the power at the sampling rate; and further including:

adjusting a selection of one of the measured current, the measured voltage, and the calculated power based upon a change in the calculated impedance.

15. The method of claim 14 further including:

wherein calculating impedance between the first and second electrodes based upon the measured current and the measured voltage includes calculating impedance at the sampling rate.

16. The method of claim 12 further including:

calculating the normalized representation of the current value based upon the measured current value and a current set point;

calculating the normalized representation of the voltage value based upon the measured voltage value and a voltage set point;

calculating the normalized representation of the power value based upon the calculated power value and a power set point; and selecting the one of the measured current, the measured voltage, and the calculated power based at least in part upon the calculated impedance and two or more of the normalized current value, the normalized voltage value and the normalized power value.

17. An electrosurgical system comprising:

a first electrode;

a second electrode;

an RF output stage configured to impart RF power between the first and second electrodes;

current measurement circuitry configured to measure current, at a sampling rate, imparted between the first and second electrodes;

voltage measurement circuitry configured to measure of voltage, at the sampling rate, imparted between the first and second electrodes;

a processing circuit configured to perform operations including:

calculating power imparted between the first and second electrodes, based upon the measured current and the measured voltage;

calculating impedance between the first and second electrodes, based upon the measured current and the measured voltage;

using a proportional-integral-derivative control loop to control RF power imparted between the electrodes, based upon a selected one of the measured current, the measured voltage, and the calculated power;

comparing the calculated impedance with a reference 5 impedance;

selecting one of a normalized current value and the normalized voltage value based upon the comparison; and comparing the selected one of the normalized current 10 value and the normalized voltage value with the normalized power value.

* * * * *